(12) United States Patent
Gu et al.

(10) Patent No.: US 9,096,493 B2
(45) Date of Patent: Aug. 4, 2015

(54) PREPARATION METHOD OF HIGH-PURITY L-CARNITINE

(75) Inventors: Shuhua Gu, Jiangshu (CN); Xuecheng Wang, Jiangshu (CN); Qingyi Li, Jiangshu (CN)

(73) Assignee: Changzhou Multiple Dimension Institute of Industry Technology Co., Ltd., Jiangsu (CN)

( * ) Notice: Subject to any disclaimer, the term of this patent is extended or adjusted under 35 U.S.C. 154(b) by 607 days.

(21) Appl. No.: 13/121,392

(22) PCT Filed: Oct. 9, 2009

(86) PCT No.: PCT/CN2009/001122
§ 371 (c)(1),
(2), (4) Date: Jul. 12, 2011

(87) PCT Pub. No.: WO2010/043110
PCT Pub. Date: Apr. 22, 2010

(65) Prior Publication Data
US 2011/0263897 A1    Oct. 27, 2011

(30) Foreign Application Priority Data
Oct. 13, 2008  (CN) .......................... 2008 1 0195331

(51) Int. Cl.
*C07C 229/22*   (2006.01)
(52) U.S. Cl.
CPC ........... *C07C 229/22* (2013.01); *C07B 2200/07* (2013.01)
(58) Field of Classification Search
CPC .......................... C07C 229/22; C07B 2200/07
USPC ....................................................... 562/567
See application file for complete search history.

(56) References Cited

FOREIGN PATENT DOCUMENTS

JP    2003-342234   *   3/2003   ............ C07C 269/00

OTHER PUBLICATIONS

Voeffray, et al. L-Carnitine. Novel Synthesis and Determination of the Optical Purity, Helvetica Chimica Acta, 70, 2058-2064 (1987).*
Spahn, H. S-(+)-Naproxen Chloride as Acylating Agent for Separating the Enantiomers of Chiral Amines and Alcohols, Arch. Pharm. (Weinheim), 321, 847-850 (1988).*
Kouzi et al. Enantiospecific Synthesis and Gas Chromatographic Resolution of (R)-(−)- and (S)-(+)-1,2-Dibromo-3-chloropropane, J. Org. Chem. 58, 771-773 (1993).*

* cited by examiner

*Primary Examiner* — Paul A Zucker
*Assistant Examiner* — Mark Luderer
(74) *Attorney, Agent, or Firm* — Squire Patton Boggs (US) LLP

(57) ABSTRACT

The present invention relate to a preparation method of high-purity L-carnitine which belongs to an important technique of quality control in different steps of chiral medicine production. The method comprises the following steps of: monitoring the content of the L-isomer impurity in chiral material S-epichlorohydrin by gas chromatography and chiral column and controlling the content of the L-isomer impurity in chiral raw material in the definite range; monitoring and controlling the specific optical rotation of the chiral intermediate L-3-chloro-2-hydroxy-N,N,N-trimethyl-propanaminium in the definite ranges using a polarimeter; monitoring the content of the R-isomer in the intermediate L-3-cyano-2-hydroxy-N,N,N-trimethyl-propanaminium using derivation agent (+)α-methyl-6-methoxy-2-naphthaleneaceyl chloride by HPLC and controlling the content of the isomer in the intermediate in the definite range; and measuring the final product L-carnitine using derivation agent (+)α-methyl-6-methoxy-2-naphthaleneaceyl chloride by HPLC. This method gives the high-purity L-carnitine in which the content of L-isomer may be more than 97% and that of R-isomer less than 2%.

16 Claims, 4 Drawing Sheets

PREPARATION METHOD OF HIGH-PURITY L-CARNITINE

FIELD OF THE INVENTION

The invention relates to a preparation method of high-purity L-carnitine. Specifically, the method is to prepare the high-purity L-carnitine by monitoring and controlling the contents of the chiral materials and the chiral intermediates.

BACKGROUND OF THE INVENTION

L-carnitine universally exists in the organs of mammal animals, and also in some plants and microorganisms. The major pharmacological effect of L-carnitine is transporting the long-chain fatty acid into the mitochondria, and thereof achieving the oxidation of fatty acid to produce energy. L-carnitine is widely used in drugs and health care products. L-carnitine was discovered in muscle extracts by Gulewitsch and Krimberg in 1905.

Natural carnitine is L-carnitine, and only L-carnitine is physiological active. L-carnitine used in current drug industry is mostly obtained by chemical synthesis. Unlike natural L-carnitine, it is difficult to obtain a totally pure L-carnitine because of the materials and synthetic route applied that D-carnitine, a dextrarotatory, is usually also obtained. D-carnitine is a competitive inhibitior of carnitine acetyl transferase (CAT) and carnitine palmityl transferase (PTC). Therefore about 10% patients suffered myasthenia gravis after taking the DL-carnitine (Martindale: the Extra Pharmacopoeia (33th): 1356). Therefore taking drug safety into consideration, it's necessary to strictly control the content of the D-carnitine in the chemical synthetic process.

Patent JP63185947 described in 1988 obtaining L-carnitine by turning a chiral epichlorohydrin to a quaternary ammonium salt, which is followed by the cyanation, hydrolysis, and demineralization reactions. It is unnecessary for this method to do the chiral separation because the starting material used for preparing L-carnitine is optically pure. However this patent mentioned neither the content of the optical isomers in the chiral materials, nor how to detect the content of L-carnitine and D-carnitine in the final product.

Patent "production of optically active quaternary ammonium salt" (JP3287567A) only described the production of the L-3-chloro-2-hydroxypropyl trimethylamine from the chiral epichlorohydrin, and mentioned the L-3-chloro-2-hydroxypropyl trimethylamine is a intermediate for optically active carnitine. The patent mentioned the optical activity of L-3-chloro-2-hydroxypropyl trimethylamine, but it did not provide the content of the optical isomers in the chiral materials nor how to detect it accurately.

The article "Synthesis of L-(−)-carnitine" (Chinese Journal of Synthetic Chemistry, vol 12, 2004) described in detail that to prepare the L-3-chloro-2-hydroxypropyl trimethylamine by amination from the chiral epichlorohydrin, then to produce the L-(−)-chloride-3-cyan-2-hydroxypropyl trimethylamine by cyanidation, and finally to obtain L-carnitine by hydrolysis, during which the specific rotation of the epichlorohydrin, the intermediate and the product was detected. However, neither the content of optical isomers in the epichlorohydrin, the intermediate and the product, nor the accurate detection was described. The method described above has quite high cost to produce pure L-carnitine. Another report about the synthesis of L-carnitine (Chinese journal of pharmaceuticals, 2006, 37(12)) provided a method that first hydrolyzing the racemic epichlorohydrin catalyzed by chiral salen-Co III complex (2) ([(R,R), N,N'-bis(3,5-di-tert-butylsalicylidene)- 1,2-cyclohexanediamino(2-)]cobalt acetate) to obtain S-epichlorohydrin, and then obtaining L-carnitine by amination, cyanidation, hydrolysis and ion exchange. It described only the specific rotation detection of the epichlorohydrin, the intermediate and the product, however, neither the content of optical isomers in the epichlorohydrin, the intermediate and the product, nor accurate detection was described. Moreover, the control method which is used to reduce the cost and raise the purity of L-carnitine was not mentioned.

The methods of detecting the content of D-carnitine in L-carnitine are as follows:

It was in J. Pharm. Biomed. Anal. 30 (2002) 209-218 reported detection of the content of D-carnitine in L-carnitine by combining HPLC with a derivatization reagent, the (+)-FLEC ((+)-1-(9-Fluoren)-ethyl chloroformate). The detection of the content of D-carnitine in the product L-carnitine was reported, however, nothing about detecting the content of enantiomer in the starting material and intermediate during the preparation of L-carnitine was reported, nor the relative control method that could be used to reduce the cost and raise the purity of L-carnitine.

Because the S-epichlorohydrin is obtained from organic synthesis or biological conversion as well, detection of the optical rotation without accurate detection of its content of the optical isomer may bring some optical isomer impurity in each step of the preparation of L-carnitine. Because there is no chiral separation during the whole preparation, the final product may possibly contain the optical isomer impurity. Furthermore, many steps are involved in the preparation of L-carnitine, so that the racemization may easily happen, Therefore accurate detection and control of the content of isomer of the starting material and accurate detection the optical purity of the intermediate in each step is necessary to ensure if racemization which affects the optical purity of the final product occurs.

Because the dextroisomer of L-carnitine is harmful to human body, it is necessary to find an effective method to make sure obtaining L-carnitine with high optical purity by detecting the optical purity of the starting materials and the intermediates and controlling the content of the optical isomer impurity in each step. This is important for ensuring human health and improving the purity of synthetic L-carnitine. Besides, concerning about the environment protection, to ensure the yield of each synthetic process and to avoid an unaccepted intermediate entering into the next reaction during the multi-synthetic steps decreases the polluting steps and reduces the cost of the "three wastes" treatment. It is also important to energy saving and emission reduction.

SUMMARY OF THE INVENTION

The object of this invention is to provide a preparation method of high-purity L-carnitine, which is characterized in that to prepare L-carnitine with a purity being above 97%, wherein the content of D-carnitine is below 2%, by detecting and controlling the content of chiral material and chiral intermediate during the whole synthetic process which is started from S-epichlorohydrin, wherein the method include the following steps:

(1) Detect the content of optical isomers of S-epichlorohydrin with GC and chiral column, and control the content of laevoisomer of S-epichlorohydrin within the range of 0%-12% W/W;

(2) Detect the specific rotation of the intermediate L-3-chloro-2-hydroxypropyl trimethylamine during the synthetic process with a polarimeter, and control the value within the range of −26.0°--29.4°;

(3) Detect the optical purity of L-3-cyan-2-hydroxypropyl trimethylamine of the intermediate mixture and the content of its dextroisomer with a chiral derivatization reagent, and control the content of the dextroisomer within the range of 0-3.6% W/W;

wherein the said chiral derivatization reagent is the optically pure D- or L-compound of formula (II):

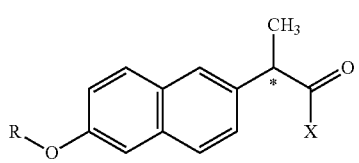

(II)

wherein, the carbon atom marked with an asterisk is the chiral carbon atom; R represents C1-C6 straight-chain or branched alkyl groups, C6-C10 aryl groups, C2-C6 straight-chain or branched alkenyl or alkynyl groups or C3-C6 cycloalkyl groups; and X represents a halogen atom.

In a preferred embodiment, the present invention provide a optically pure compound of formula (II) wherein R represents methyl, ethyl, isopropyl, butyl or benzyl, and X represents Cl or Br.

More preferably, the optically pure compound of formula (II) in the present invention is crystalline solid. Wherein the crystalline solid compound is preferably selected from: (+)α-methyl-6-methoxy-2-naphthyl acetyl chloride, (−)α-methyl-6-methoxy-2-naphthyl acetyl chloride, (+)α-methyl-6-ethoxy-2-naphthyl acetyl chloride and (−)α-methyl-6-ethoxy-2-naphthyl acetyl chloride.

Most preferably, the optically pure compound of formula (II) in the present invention is selected from (+)α-methyl-6-methoxy-2-naphthyl acetyl chloride, (+)α-methyl-6-ethoxy-2-naphthyl acetyl chloride and their crystalline.

In a preferred embodiment, the detection of the optical purity of L-3-cyano-2-hydroxypropyl trimethyl ammoniumin and the content of its dextroisomer in step (3) of the present invention includes the following steps:

(1) Preparation of the derivatization reagent solution: D-type or L-type optical pure compound of formula (II) is dissolved in solvent to prepare a 0.01-100 mg/ml solution under the dark conditions;

(2) Preparation of the test solution: Proper amount of L-3-cyano-2-hydroxypropyl trimethyl ammonium sample is hydrolyzed with hydrochloric acid and then the aqua ammonia is added in to adjust the pH value until it is neutral;

(3) Preparation of the control solution: Proper amount of racemic carnitine is used to prepare the control solution;

(4) Derivatization reaction: Proper amount of optically pure derived reagent of formula (II) is mixed with L-carnitine (or D-carnitine) test solution and carnitine control solution. The derivatization reagent from the above step (1) is reacted with the test solution from above step (2) and the control solution from above step (3) respectively in the present of solvent at 20° C.-95° C., so that to produce L-carnitine and D-carnitine derivatives;

(5) the content of L-carnitine and D-carnitine in test solution and control solution from the above step (4) is detected with HPLC, and the content of L-isomer L-3-cyano-2-hydroxypropyl trimethyl ammonium and D-isomer D-3-cyano-2-hydroxypropyl trimethyl ammonium is calculated thereby.

DETAILED DESCRIPTION OF THIS INVENTION

The synthesis technology of L-carnitine which is started from S-epichlorohydrin (as shown in reaction formula I) provides a series of crucial quality control technique in different preparation steps, which can raise the optical purity of L-carnitine, reduce the content of harmful D-carnitine, low the cost effectively. It is a preparation method of high-purity L-carnitine.

1, Detect the content of optical isomer of S-epichlorohydrin with GC and chiral column, and control the content of laevoisomer of S-epichlorohydrin within the range of 0%-12% W/W, so that the purity of L-carnitine is above 97%, and the content of D-carnitine is below 2%.

2, Control the specific rotation of the intermediate L-3-chloro-2-hydroxypropyl trimethylamine during the synthetic process within the range of −26.0°−−29.4° with a polarimeter, so that the purity of L-carnitine is above 97%, and the content of D-carnitine is below 2%.

3, Detect the optical purity of L-3-cyan-2-hydroxypropyl trimethylamine and the content of its dextroisomer with the chiral derivatization reagent in the present invention, and control the content of the dextroisomer within the range of 0-3.6% W/W, so that the purity of L-carnitine is above 97%, and the content of D-carnitine is below 2%.

The synthesis technology of L-carnitine in the present invention is:

It is started from S-epichlorohydrin, which is firstly used to produce a L-quaternary ammonium salt (L-chloro-3-chloro-2-hydroxypropyl trimethylamine) by the amination of trimethylamine hydrochloride, the quaternary ammonium salt is then cyanided with NaCN to produce a L-cyanide (L-chloro-3-cyan-2-hydroxypropyl trimethylamine), the cyanide is then hydrolyzed with concentrated hydrochloric acid to produce L-carnitine hydrochloride, the L-carnitine hydrochloride is finally used to produce L-carnitine product by electrodialysis desalination, concentration and refine.

L-carnitine synthesis of the present invention also includes the same synthetic process above which is started from L-quaternary ammonium or L-cyanide.

Reaction formula:

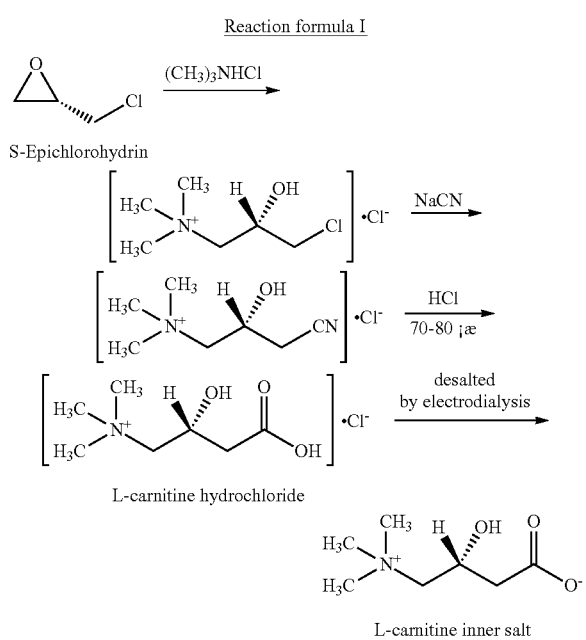

Reaction formula I

L-carnitine hydrochloride

L-carnitine inner salt

The present invention discloses sensitive detection of the optical purity of S-epichlorohydrin, characterized by the use of chiral derivatization reagent, gas chromatography and chiral column, it is especially preferably selected the ZT chiral column from the ZKAT company (0.25×0.5×20, the production serial number is 08-01-001), the inlet temperature is 120 to 180° C., the column temperature is 80 to 100° C., and the detector temperature is 200 to 240° C., the carrier gas is nitrogen gas with split ratio of 4:1.

Optically pure compound of formula (II) is preferably the crystalline solid. A solution of the optically pure compound of formula (II) with certain concentration can also be used. Wherein the solvent is selected from: ether, propyl ether, tetrahydrofuran, acetone, methyl ethyl ketone, acetonitrile, propionitrile, ethyl acetate, n-hexane, dichloromethane, chloroform, or the mixture of any two or more solvents above; The concentration of the solution is 0.01-100 mg/ml. Specially preferably, the solvent is acetonitrile and the concentration of the solution is 1-10 mg/ml.

The present invention also discloses the detection of the optical purity of L-3-cyano-2-hydroxypropyl trimethyl ammonium and the content of its D-isomer in the intermediate mixture, wherein the detection method includes the following steps:

(1) Preparation of the derivatization reagent solution: D-type or L-type optical pure compound of formula (II) is dissolved in solvent above to prepare a 0.01-100 mg/ml solution under the dark conditions. Preferably, the optical pure compound of formula (II) is (+)α-methyl-6-methoxy-2-naphthyl chloride, the solvent is acetonitrile, and the concentration of the solution is 1-10 mg/ml.

(2) Preparation of the test solution: Proper amount of L-3-cyano-2-hydroxypropyl trimethyl ammonium sample is hydrolyzed with hydrochloric acid. Preferably, the weight/volume ratio of nitrile and 30% HCl is 27.5 g:40 ml. The mixture is heated at 70° C.-80° C. for 5 hours, cooled to room temperature, and then the aqua ammonia is added in to adjust the PH value until it is neutral.

(3) Preparation of the control solution: Proper amount of racemic carnitine is used to prepare the control solution.

(4) Derivatization reaction: Proper amount of optically pure derived reagent of formula (II) is mixed with L-carnitine (or D-carnitine) test solution and carnitine control solution. The derivatization reagent from the above step (1) is reacted with the test solution from above step (2) and the control solution from above step (3) respectively in the present of solvent at 20° C.-95° C., so that to produce L-carnitine and D-carnitine derivatives.

(5) HPLC detection: the content of L-carnitine and D-carnitine in test solution and control solution from the above step (4) is detected with HPLC, and the content of L-isomer L-3-cyano-2-hydroxypropyl trimethyl ammonium and D-isomer D-3-cyano-2-hydroxypropyl trimethyl ammonium is calculated thereby.

The present invention also discloses detection of the content of L-carnitine and D-carnitine of the final product by using the chiral HPLC method and the derivatization reagent, wherein the test sample is dissolved to form test solution directly without the need of hydrolysis.

The preparation method of high-purity L-carnitine that applies the crucial quality control technique in different preparation steps is used to provide a high-purity L-carnitine, wherein the content of L-carnitine is above 97%, while content of D-carnitine is below 2%. So that not only is the harm of D-carnitine impurity produced in the synthetic process of L-carnitine to human controlled effectively, but the cost of production is greatly reduced and quality of the product is improved because of the precise control of the start materials and the impurities and product of reactant.

EXAMPLES

Figure 1:
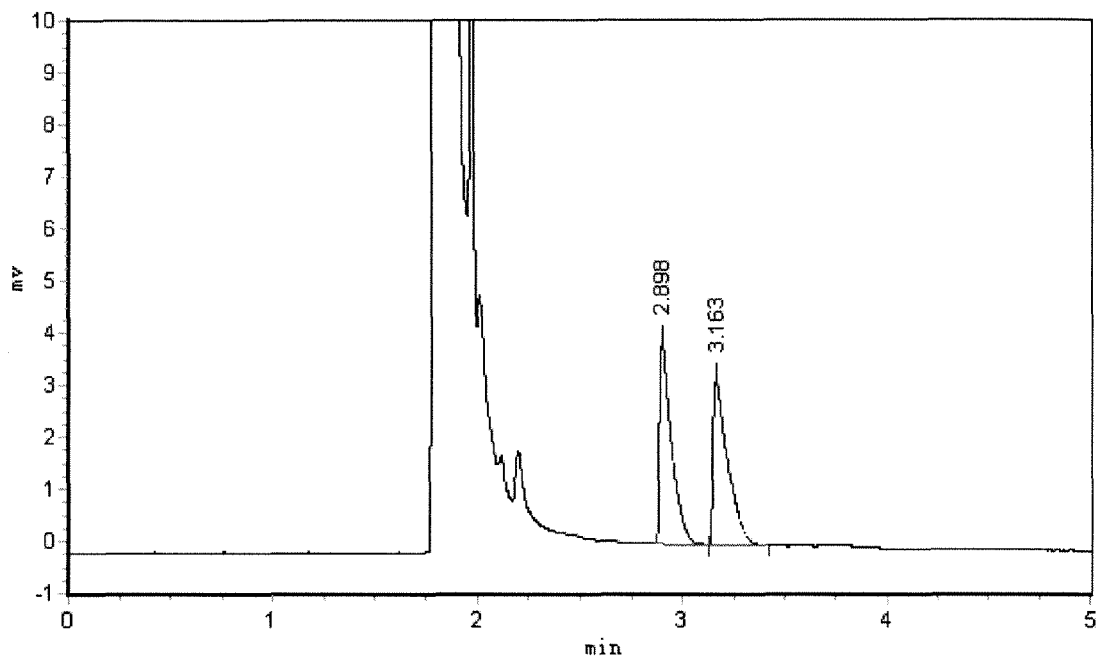
FIG. 1 is the chromatogram of detecting the optical purity of racemic epichlorohydrin

The following examples are only for illustration of the invention and shall not be construed to limit the scope of the present invention.

Example 1

Establish the Detecting Method of the Optical Purity of Epichlorohydrin with Gas Chromatography (1) Choosing the Chiral Gas Chromatographic Column
The chiral columns supplied by different manufacturers are tested during the method establishment; different columns are listed in Table 1.

TABLE 1 the experimental data for choosing chiral column that detecting the optical purity of epichlorohydrin

| The Model of Chiral Column | Supplier | Parameters of Chiral column | Resolution |
| --- | --- | --- | --- |
| CHIRALDEX B-PM | Nanjing Kejie Analytical Instrument Co., Ltd | 30 × 0.25 | 0.21 |
| FS-LIPODEX ® A | MACHEREY-NAGEL Co., Ltd, Germany | 50 × 0.25 mm ID | 0.78 |
| ZT Chiral Column | Atech Technologies Co., Ltd | 0.25 × 0.5 × 20 | 1.87 |
| CHIRALDEX B-DA | Tianjin Brilliant Technology Co., LTD | 30 × 0.25 | 0.12 |

By the comparing test, we found that only the ZT chiral column supplied by Atech Technologies Co., Ltd could separate the levo epichlorohydrin from dextro epichlorohydrin well. The resolution was 1.87 which matched the requirements.

The parameters of the ZT chiral column supplied by Atech Technologies Co., Ltd are as follow:

The ZT chiral column was purchased from Atech Technologies Co., Ltd; the maximum operating temperature is 200° C.;

The stationary liquid is ZKAT-chiral B; the execution standard is Q/ZKAT01-2005;

Production serial number is 08-01-001; Art. No is 802103-4;

(2) Chromatographic Conditions

Injection temperature: 150° C.; column temperature: 85° C.; detection temperature: 220° C.;

Carrier gas: $N_2$; inlet pressure: 0.04 MPa (15.9 ml/min); make-up gas pressure: 0.12 MPa $H_2$: 0.1 MPa; air: 0.08 MPa;

Split rate: 47 ml/min (measured with a bubble flow meter); split ratio=4:1

Sampling concentration: the sample was diluted with ether for 250 times; sampling volume: 1 μL (3) The Limit of Detection The racemic epichlorohydrin was canceled, ether was use as the solvent to prepare five sample solutions with concentrations of 0.004 μl/ml, 0.008 μl/ml, 0.016 μl/ml, 0.024 μl/ml and 0.032 μl/ml, and they were detected successively.

The result was the SNR of 0.032 μl/ml (R)-epichlorohydrin chromatographic was about 3:1. That is detection limit concentration of (R)-epichlorohydrin was 0.016 μl/ml. The detection limit was $1.6 \times 10^{-5}$ μl because the sampling volume was 1 μl.

Example 2

Detection of the Content of the D-Isomer of the Intermediate (L-3-Cyano-2-Hydroxypropyl Trimethyl Ammonium)

L-3-cyano-2-hydroxypropyl trimethyl ammonium (27.5 mg) was weighted precisely and put in 100 mL volumetric flask, 30% hydrochloric acid (40 μL) was added in. After hydrolysis at 75° C. for 5 h, the aqua ammonia was dripped in to adjust the PH value to 7.0, water is added to volume. 10 ml solution is pipeted to 100 ml volumetric flask precisely again, and water is added to volume. It was the test solution.

DL-carnitine (20 mg) was weighted precisely and put in 100 mL volumetric flask and dissolved with water which is added to volume as well. 1 ml solution is pipeted to 100 ml volumetric flask precisely again, and water is added to volume. It was the control solution.

The control solution (30 μL) and the test solution (5 mL) was pipeted to brown volumetric flask respectively, and 30 μL of 0.05 mol/L carbonate buffer (pH=10.3), 100 ul of pyridine acetonitrile solution (each 1 ml acetonitrile contained pyridine 5 ul) and 100 μL of 0.5% derivatization reagent was added respectively and mixed. After sealed and reacted at 60° C. in water bath for 90 min, it was taken out and diluted with 0.05 mol/L acetic acid buffer (pH=4.0) to scale, and was filtered. 10 ul of the test sample and control sample derived was pipeted precisely and injected in the liquid chromatograph. The chromatograms were recorded. And the content of D-isomer was calculated with external method and peak area method.

HPLC detection method was as follows:

Agilent 1100 HPLC; the fluorescence detector; the column: C18-ODS column (4.6×150 mm, 5 μm); the total flow rate: 1 ml/min; mobile phase is the triethylamine buffer solution (8 ml of phosphate, 15 ml of triethylene amine, 1500 ml of water, pH adjusted to 5.4)—tetrahydrofuran (THF) mixture, the time gradient is listed in the following Table 2:

TABLE 2

HPLC gradient time table

| Time (min) | Triethylamine buffer solution (%) | THF (%) |
|---|---|---|
| 0 | 75 | 25 |
| 10 | 75 | 25 |
| 11 | 30 | 70 |
| 18 | 30 | 70 |
| 19 | 75 | 25 |
| 25 | 75 | 25 |

The content of D-isomer of L-3-cyano-2-hydroxypropyl trimethyl ammonium detected is showed in table 3

TABLE 3

The results of the content of D-isomer of L-3-cyano-2-hydroxypropyl Trimethyl Ammonium

| | 1 | 2 | 3 | 4 | 5 | 6 | Average | RSD |
|---|---|---|---|---|---|---|---|---|
| D-isomer (%) | 1.22 | 1.26 | 1.20 | 1.25 | 1.23 | 1.23 | 1.23 | 1.74% |

Example 3

Preparation of L-Carnitine Started from S-Epichlorohydrin Having Different Optical Purity Step 1 Preparation of L-3-Chloro-2-Hydroxypropyl Trimethylammonium Firstly, the content of L-isomer of S-epichlorohydrin was detected according to the method of example 1 above.

Secondly, trimethylamine solution (60 g) was added in 250 ml three-necked flask, stirred and cooled to 10-20° C., after S-epichlorohydrin (35 g) being dripped in, the mixture was stirred and kept at 10-20° C. for 2-4 hours, and then the reacting temperature was raised to and kept at 30-70° C. for 2 to 4 hours, evaporated to appropriate amount under a reduced pressure, crystallized by freezing, then dried to give L-3-chloro-2-hydroxypropyl trimethyl ammonium (55.2 g), yield 89.0%, m.p. 212.0° C.-215.6° C. The optical rotation was detected with the polarimeters.

Step 2 Preparation of L-3-Cyano-2-Hydrooxypropyl Trimethylammonium

L-3-chloro-2-hydroxypropyl trimethyl ammonium (50 g) was added in 250 ml three-necked flask, dissolved in H2O (40 ml), heated at 30° C.-70° C., sodium cyanide (48 g) was dripped, kept at 70° C. for 4 hours, evaporated under a reduced pressure, freezed below 0° C., and dried to give L-3-cyano-2-hydroxypropyl trimethyl ammonium (43.8 g), yield 92.1%, m.p. 252.8° C.-253.4° C.

Step 3 Preparation of L-Carnitine

L-3-cyano-2-hydroxypropyl trimethyl ammonium (27.5 g) and 30% hydrochloric acid (40 ml) was added in 205 ml flask, heated at 70° C.-80° C., and kept for 5 hours. After that, the excess hydrochloric acid was evaporated under reduced pressure at 70° C., the residue was then cooled to 20° C., added 20% ammonia (20 g), cooled to 0° C., the ammonium chloride was filtered off. Activated carbon (3 g) was added to the mother liquor, decolored, desalted and evaporated to dryness under reduced pressure, then ethanol (50 ml) was added, refluxed for 1 hour at 50° C.-80° C., cooled to 20° C., acetone was dripped (125 ml), filtrated and dried to give L-carnitine product (18.6 g), yield 75.4%.

Results:

The experimental data of preparation L-carnitin from S-epichlorohydrin with different optical purity is listed in Table 4:

TABLE 4

| Number | S-Epichlorohydrin samples | The content of R-enantiomeric of S-Epichlorohydrin/% | The content of D-enantiomeric of L-carnitine/% | The content of L-enantiomeric/% | yield/% |
|---|---|---|---|---|---|
| 1 | epichlorohydrin applied by Shenzhen Asiatop Carnitine Technology Co., Ltd | 1.73 | 0.42 | 99.1 | 62.4 |
| 2 | epichlorohydrin applied by Shanghai KeLy Bio-Pharmaceutical Co., Ltd | 0.38 | 0.26 | 99.5 | 62.8 |
| 3 | epichlorohydrin having 10% Racemic | 6.52 | 0.95 | 98.3 | 61.9 |
| 4 | epichlorohydrin having 20% Racemic | 11.58 | 1.92 | 97.1 | 62.0 |

Figure 6:
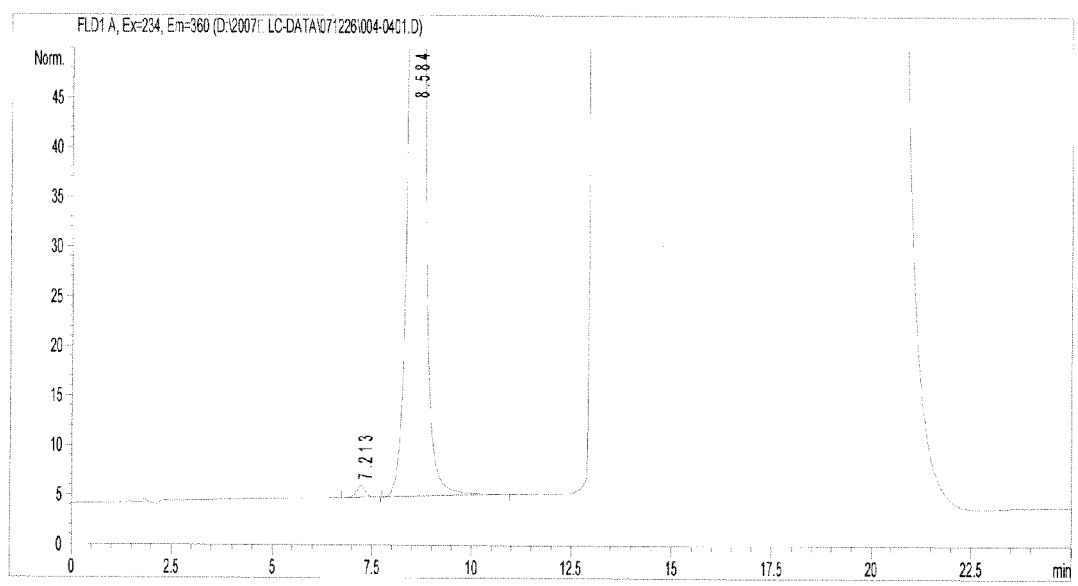
FIG. 6 is the HPLC of the D-isomer of L-carnitine which is prepared by S-epichlorohydrin from Shenzheng.
Figure 7:
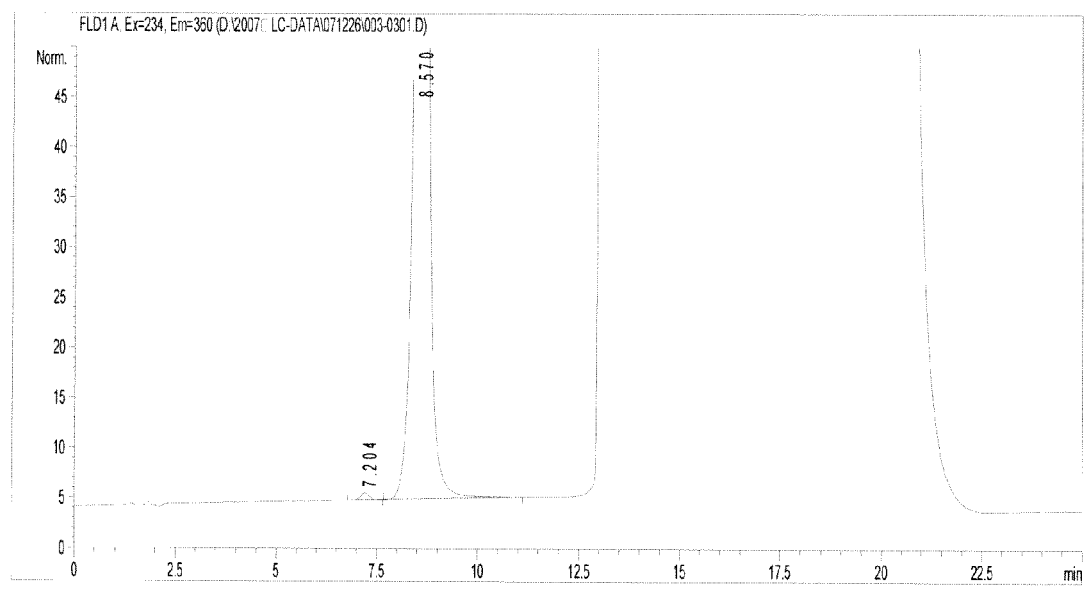
FIG. 7 is the HPLC of the D-isomer of L-carnitine which is prepared by S-epichlorohydrin from Shanghai.

The content of S-enantiomeric and R-enantiomeric of S-Epichlorohydrin having different optical purity is showed in FIG. 1-5. The HPLC of dextroisomer of L-carnitine is showed in FIG. 6-7.

The data related to FIG. 1-5 is listed in table 5-9:

TABLE 5 the data related to FIG. 1

| Peak number | name | Retention time | Peak height | Peak area | Content |
|---|---|---|---|---|---|
| 1 | R-Epichlorohydrin | 2.898 | 3829.946 | 16227.346 | 50.1291 |
| 2 | S-Epichlorohydrin | 3.163 | 3149.135 | 16143.754 | 49.8709 |
| Total | | | 6979.081 | 32371.100 | 100.0000 |

Figure 2:
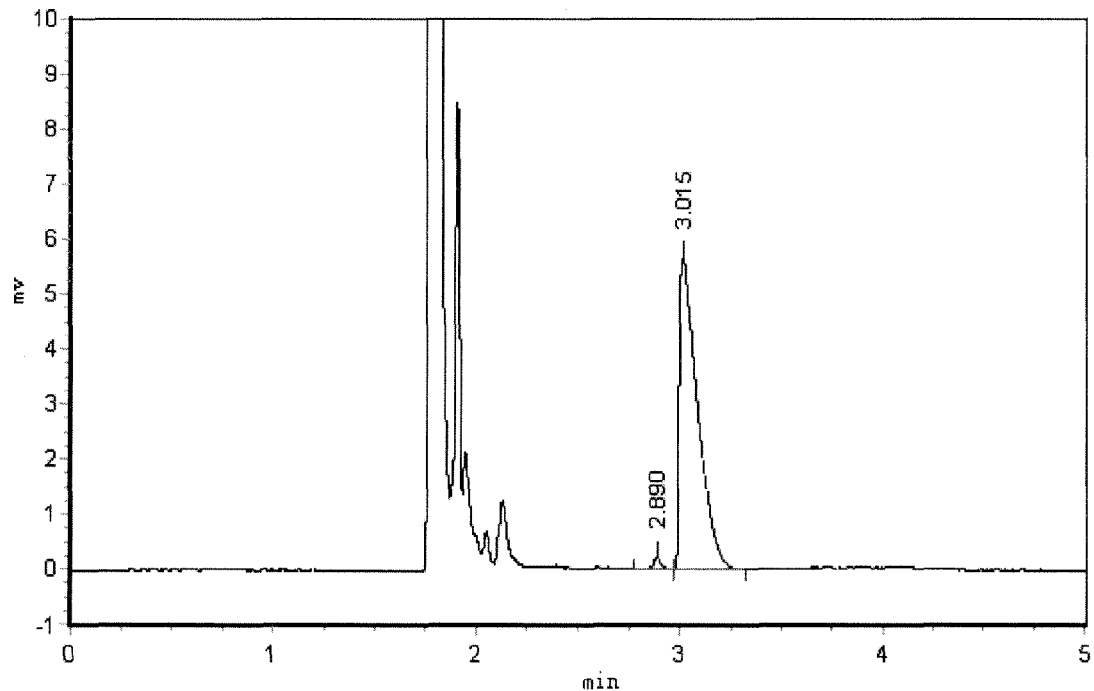
FIG. 2 is the gas chromatogram of detecting the optical purity of S-epichlorohydrin which is from Shenzheng YaWang-kangli.

TABLE 6 the data related to FIG. 2

| Peak number | name | Retention time | Peak height | Peak area | Content |
|---|---|---|---|---|---|
| 1 | R-Epichlorohydrin | 2.890 | 203.576 | 633.192 | 1.7296 |
| 2 | S-Epichlorohydrin | 3.015 | 5645.121 | 35975.609 | 98.2704 |
| Total | | | 5848.697 | 36608.802 | 100.0000 |

Figure 3:
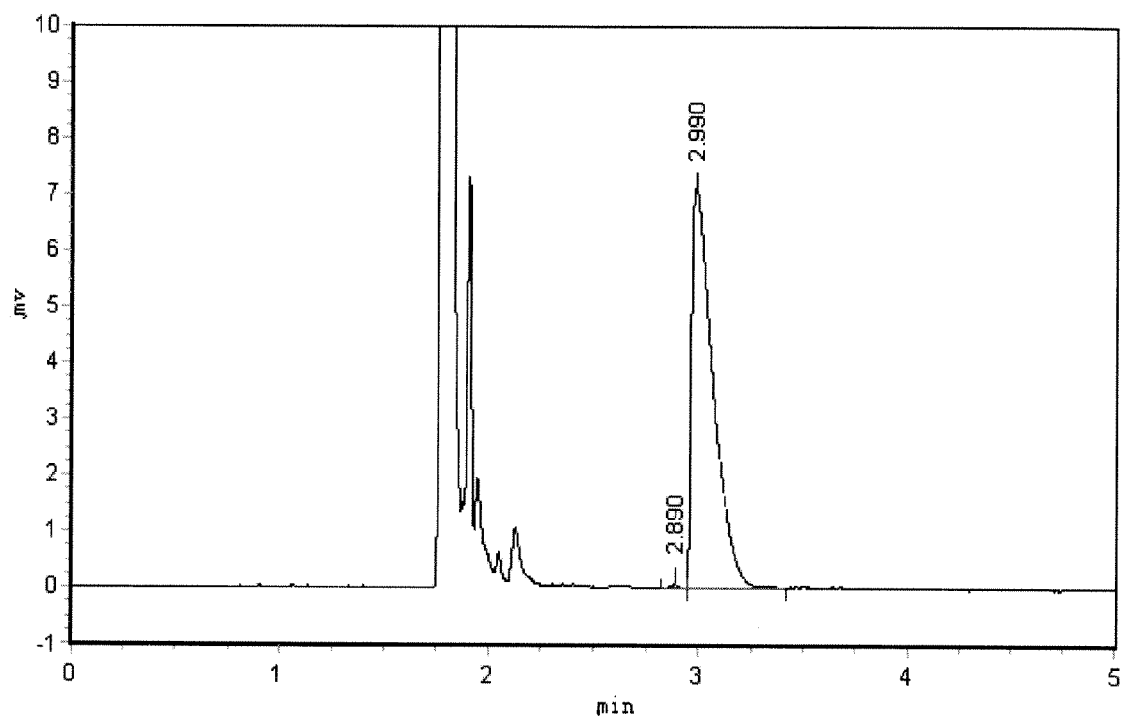
FIG. 3 is the gas chromatogram of detecting the optical purity of S-epichlorohydrin which is from Hai Keli biopharm.

TABLE 7 the data related to FIG. 3

| Peak number | name | Retention time | Peak height | Peak area | Content |
|---|---|---|---|---|---|
| 1 | R-Epichlorohydrin | 2.890 | 58.222 | 191.331 | 0.3775 |
| 2 | S-Epichlorohydrin | 2.990 | 7110.056 | 50491.469 | 99.6225 |
| Total | | | 7168.278 | 50682.800 | 100.0000 |

Figure 4:
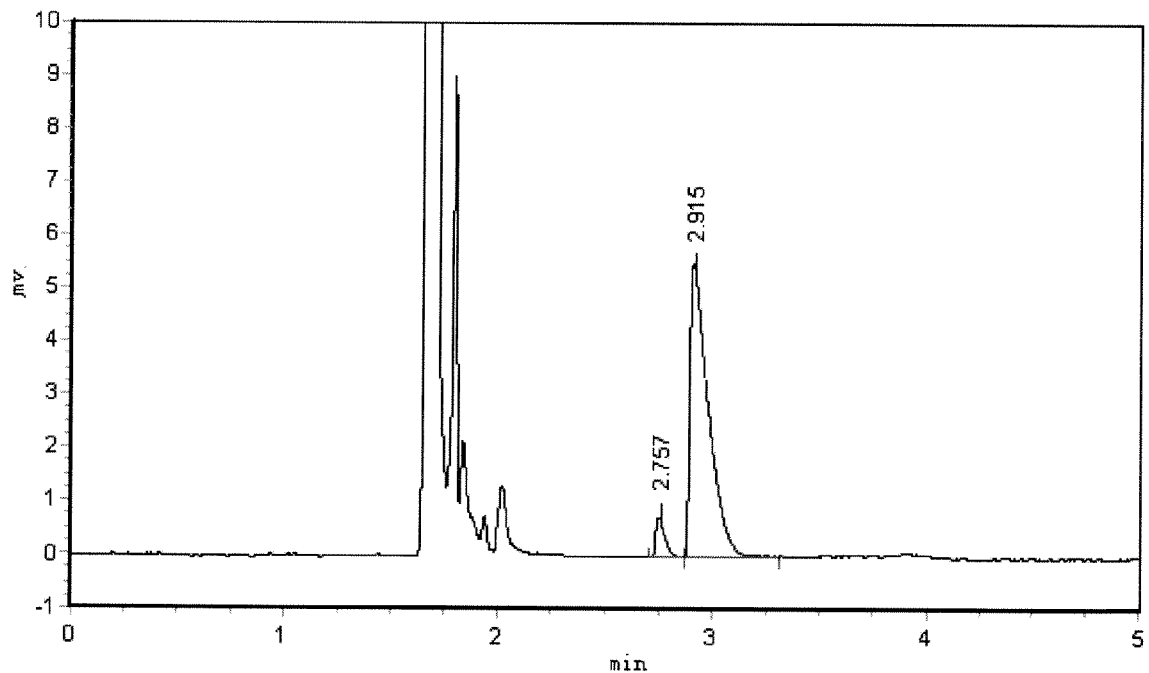
FIG. 4 is the gas chromatogram of detecting the optical purity of epichlorohydrin which 10% racemes is added.

TABLE 8 the data related to FIG. 4

| Peak number | name | Retention time | Peak height | Peak area | Content |
|---|---|---|---|---|---|
| 1 | R-Epichlorohydrin | 2.757 | 732.945 | 2318.192 | 6.5203 |
| 2 | S-Epichlorohydrin | 2.915 | 5477.438 | 33235.359 | 93.4797 |
| Total | | | 6210.384 | 35553.552 | 100.0000 |

Figure 5:
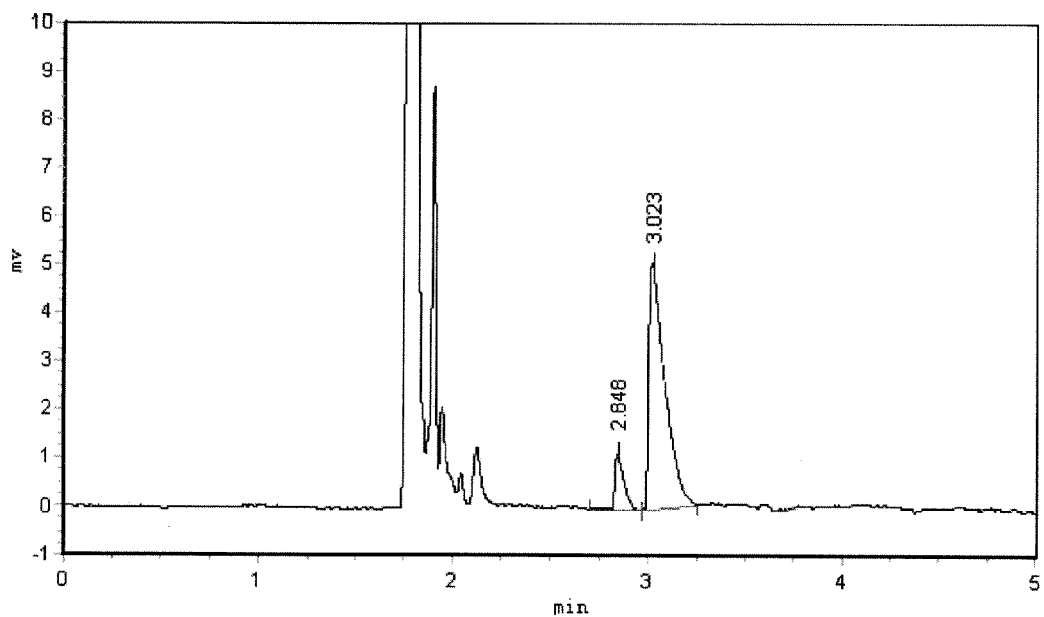
FIG. 5 is the gas chromatogram of detecting the optical purity of epichlorohydrin which 20% racemes is added

TABLE 9 the data related to FIG. 5

| Peak number | name | Retention time | Peak height | Peak area | Content |
|---|---|---|---|---|---|
| 1 | R-Epichlorohydrin | 2.848 | 1144.774 | 3841.400 | 11.574 |
| 2 | S-Epichlorohydrin | 3.023 | 5028.600 | 29348.500 | 88.4260 |
| Total | | | 6173.374 | 33189.900 | 100.0000 |

Example 4

Preparation of L-Carnitine from L-3-Chloro-2-Hydroxypropyl Trimethylammonium

L-carnitine was prepared from L-3-chloro-2-hydroxypropyl trimethylammonium having different optical purity in step 2 according the method of example 3. The experimental data is listed in table 10.

TABLE 10

The example data of preparation of L-carnitine from L-3-chloro-2-hydroxypropyl trimethylammonium having different optical purity

| Serial number | specific rotation of L-3-chloro-2-hydroxypropyl trimethylammonium | D-iomeric of carnitine/% | L-iomeric of carnitine/% | yield/% |
|---|---|---|---|---|
| 1 | −28.7° | 0.42 | 99.0 | 69.8 |
| 2 | −29.3° | 0.23 | 99.6 | 70.5 |

TABLE 10-continued

The example data of preparation of L-carnitine from L-3-chloro-2-hydroxypropyl trimethylammonium having different optical purity

| Serial number | specific rotation of L-3-chloro-2-hydroxypropyl trimethylammonium | D-iomeric of carnitine/% | L-iomeric of carnitine/% | yield/% |
|---|---|---|---|---|
| 3 | −27.5° | 0.94 | 98.1 | 70.1 |
| 4 | −26.1° | 1.89 | 97.4 | 69.5 |

Example 5

Preparation of L-Carnitine from L-3-Cyano-2-Hydroxypropyl Trimethylammonium

L-carnitine was prepared from L-3-cyano-2-hydroxypropyl trimethylammonium having different optical purity in step 3 according the method of example 3. The experimental data is listed in table 11.

TABLE 11

The example data of preparation of L-carnitine from L-3-cyano-2-hydroxypropyl trimethylammonium having different optical purity

| Serial number | specific rotation of L-3-chloro-2-hydroxypropyl trimethylammonium | D-iomeric of carnitine/% | L-iomeric of carnitine/% | yield/% |
|---|---|---|---|---|
| 1 | 0.78 | 0.40 | 99.1 | 75.8 |
| 2 | 0.41 | 0.28 | 99.4 | 76.2 |
| 3 | 1.9 | 0.95 | 98.3 | 75.4 |
| 4 | 3.6 | 1.87 | 97.5 | 75.6 |

The invention claimed is:

1. A method for preparing a high-purity L-carnitine, characterized in that the L-carnitine has a purity above 97% and the content of D-carnitine is below 2%, by detecting and controlling the content of chiral materials and chiral intermediates during the whole synthetic process which starts from S-epichlorohydrin, wherein the method comprising the following steps:

(a) detecting the content of optical isomers of S-epichlorohydrin with gas chromatography (GC) with a chiral column, and controlling the content of laevoisomer of S-epichlorohydrin within the range from 0% to 12% w/w;

(b) detecting the specific rotation of the intermediate L-3-chloro-2-hydroxypropyl trimethylamine during the synthetic process with a polarimeter, and controlling the value within the range from −26.0°-−29.4°; and (c) detecting the optical purity of L-3-cyano-2-hydroxypropyl trimethylamine of the intermediate mixture and the content of its dextroisomer with a chiral derivatization reagent, and controlling the content of the dextroisomer within the range from 0-3.6% w/w;

wherein the chiral derivatization reagent is a optically pure D- or L-compound of formula (II):

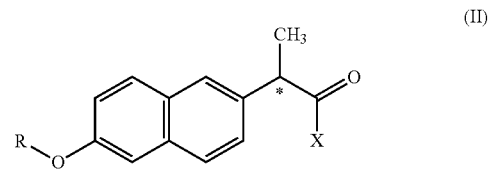

wherein:
the carbon atom marked with an asterisk is the chiral carbon atom;
R represents C1-C6 straight-chain or branched alkyl groups, C6-C10 aryl groups, C2-C6 straight-chain or branched alkenyl or alkynyl groups or C3-C6 cycloalkyl groups; and
X represents a halogen atom.

2. The method according to claim 1, wherein, in the optically pure compound of formula (II), R represents methyl, ethyl, isopropyl, butyl or benzyl; and X represents Cl or Br.

3. The method according to claim 1, wherein optically pure compound of formula (II) is a crystalline solid.

4. The method according to claim 1, wherein the optically pure compound of formula (II) is selected from (+)α-methyl-6-methoxy-2-naphthyl acetyl chloride, (−)α-methyl-6-methoxy-2-naphthyl acetyl chloride, (+)α-methyl-6-ethoxy-2-naphthyl acetyl chloride and (−)α-methyl-6-ethoxy-2-naphthyl acetyl chloride.

5. The method according to claim 4, wherein the optically pure compound of formula (II) is (+)α-methyl-6-methoxy-2-naphthyl acetyl chloride.

6. The method according to any of claims 1 to 5, wherein the derivatization reagent is dissolved in a solvent so as to form a solution with concentration of 0.01-100 mg/ml, wherein the solvent is selected from ether, propyl ether, tetrahydrofuran, acetone, methyl ethyl ketone, acetonitrile, propionitrile, ethyl acetate, n-hexane, dichloromethane, chloroform, or their mixture of any two or more.

7. The method according to claim 6, wherein the solvent is acetonitrile, and the concentration is from 1-10 mg/ml.

8. The method according to claim 1, wherein detecting the optical purity of L-3-cyano-2-hydroxypropyl trimethyl ammonium and the content of its D-isomer in step (c) comprises the following steps:

(A) preparing the solution of the derivatization reagent where the D-type or L-type optical pure compound of formula (II) is dissolved in solvent to prepare a 0.01-100 mg/ml solution under dark conditions;

(B) preparing the test solution where a proper amount of L-3-cyano-2-hydroxypropyl trimethyl ammonium sample is hydrolyzed with hydrochloric acid and then the aqua ammonia is added in to adjust the pH value until it is neutral;

(C) preparing the control solution where a proper amount of racemic carnitine is used to prepare the control solution;

(D) causing the proper amount of optically pure derived reagent of formula (II) to be mixed the with L-carnitine (or D-carnitine) test solution and the carnitine control solution; thereby the derivatization reagent from above step (A) reacts with the test solution from above step (B) and the control solution from above step (C) respectively in the present of solvent at 20° C.-95° C. to generate L-carnitine and D-carnitine derivatives;

(E) detecting the content of L-camitine and D-camitine in the test solution and control solution from the above step (D) with high performance liquid chromatography (HPLC), whereby the content of L-isomer L-3-cyano-2-hydroxypropyl trimethyl ammonium and D-isomer D-3-cyano-2-hydroxypropyl trimethyl ammonium is calculated.

9. A method for preparing a high-purity L-camitine, characterized in that the L-camitine has a purity above 97% and the content of D-camitine is below 2%, by detecting and controlling the content of chiral materials and chiral intermediates during the whole synthetic process which starts from S-epichlorohydrin, wherein the method comprising the following steps:
   (a) detecting the content of optical isomers of S-epichlorohydrin with gas chromatography (GC) with a chiral column, and controlling the content of laevoisomer of S-epichlorohydrin within the range from 0% to 12% w/w;
   (b) detecting the specific rotation of the intermediate L-3-chloro-2-hydroxypropyl trimethylamine during the synthetic process with a polarimeter, and controlling the value within the range from −26.0° to −29.4°; and
   (c) detecting the optical purity of L-3-cyano-2-hydroxypropyl trimethylamine of the intermediate mixture and the content of its dextroisomer with a chiral derivatization reagent, and controlling the content of the dextroisomer within the range from 0 to 3.6% w/w;
   wherein the chiral derivatization reagent is a optically pure D- or L-compound of formula (II):

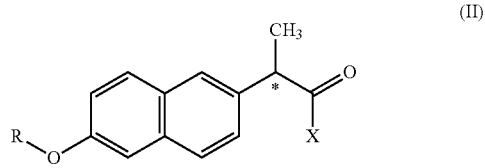

(II)

wherein:
the carbon atom marked with an asterisk is the chiral carbon atom;
R represents C2-C6 straight-chain or branched alkyl groups, C6-C10 aryl groups, C2-C6 straight-chain or branched alkenyl or alkynyl groups or C3-C6 cycloalkyl groups; and
X represents a halogen atom.

10. The method according to claim 9, wherein, in the optically pure compound of formula (II), R represents ethyl, isopropyl, butyl or benzyl; and X represents Cl or Br.

11. The method according to claim 9, wherein optically pure compound of formula (II) is a crystalline solid.

12. The method according to claim 9, wherein the optically pure compound of formula (II) is selected from (+)α-methyl-6-ethoxy-2-naphthyl acetyl chloride and (−)α-methyl-6-ethoxy-2-naphthyl acetyl chloride.

13. The method according to claim 12, wherein the optically pure compound of formula (II) is (+)α-methyl-6-ethoxy-2-naphthyl acetyl chloride.

14. The method according to claim 9, wherein the derivatization reagent is dissolved in a solvent so as to form a solution with concentration of 0.01-100 mg/ml, wherein the solvent is selected from ether, propyl ether, tetrahydrofuran, acetone, methyl ethyl ketone, acetonitrile, propionitrile, ethyl acetate, n-hexane, dichloromethane, chloroform, or their mixture of any two or more.

15. The method according to claim 14, wherein the solvent is acetonitrile, and the concentration is from 1 to 10 mg/ml.

16. The method according to claim 9, wherein detecting the optical purity of L-3-cyano-2-hydroxypropyl trimethyl ammonium and the content of its D-isomer in step (c) comprises the following steps:
   (A) preparing the solution of the derivatization reagent where the D-type or L-type optical pure compound of formula (II) is dissolved in solvent to prepare a 0.01-100 mg/ml solution under dark conditions;
   (B) preparing the test solution where a proper amount of L-3-cyano-2-hydroxypropyl trimethyl ammonium sample is hydrolyzed with hydrochloric acid and then the aqua ammonia is added in to adjust the pH value until it is neutral;
   (C) preparing the control solution where a proper amount of racemic camitine is used to prepare the control solution;
   (D) causing the proper amount of optically pure derived reagent of formula (II) to be mixed the with L-carnitine (or D-camitine) test solution and the carnitine control solution; thereby the derivatization reagent from the above step (A) reacts with the test solution from above step (B) and the control solution from above step (C) respectively in the present of solvent at 20° C.-95° C. to generate L-camitine and D-carnitine derivatives;
   (E) detecting the content of L-carnitine and D-carnitine in the test solution and control solution from the above step (D) with high performance liquid chromatography (HPLC), whereby the content of L-isomer L-3-cyano-2-hydroxypropyl trimethyl ammonium and D-isomer D-3-cyano-2-hydroxypropyl trimethyl ammonium is calculated.

* * * * *